(12) United States Patent
Dirix

(10) Patent No.: US 9,347,892 B2
(45) Date of Patent: May 24, 2016

(54) OPTICAL INSPECTION APPARATUS AND OPTICAL SORTING APPARATUS

(71) Applicant: Visys NV, Hasselt (BE)

(72) Inventor: Bert Dirix, Linter (BE)

(73) Assignee: Visys NV, Hasselt (BE)

( * ) Notice: Subject to any disclaimer, the term of this patent is extended or adjusted under 35 U.S.C. 154(b) by 0 days.

(21) Appl. No.: 14/415,896

(22) PCT Filed: Jul. 15, 2013

(86) PCT No.: PCT/IB2013/055820
§ 371 (c)(1),
(2) Date: Jan. 20, 2015

(87) PCT Pub. No.: WO2014/013421
PCT Pub. Date: Jan. 23, 2014

(65) Prior Publication Data
US 2015/0219570 A1      Aug. 6, 2015

(30) Foreign Application Priority Data
Jul. 20, 2012   (BE) .................................. 2012/0506

(51) Int. Cl.
*G01N 21/00*       (2006.01)
*G01N 21/89*       (2006.01)
(Continued)

(52) U.S. Cl.
CPC .......... *G01N 21/8901* (2013.01); *B07C 5/3425* (2013.01); *B07C 5/363* (2013.01); *B07C 2501/0018* (2013.01); *G01N 2021/845* (2013.01); *G01N 2021/8908* (2013.01)

(58) Field of Classification Search
CPC .......... G01N 21/9501; G01N 21/8806; G01N 21/94; G01N 21/956; G01N 21/88
USPC ...................................................... 356/237.1
See application file for complete search history.

(56) References Cited

U.S. PATENT DOCUMENTS 4,889,241 A   12/1989   Cogan et al.
5,352,888 A   10/1994   Childress
(Continued)

FOREIGN PATENT DOCUMENTS

AU          605209        6/1988
BE       1013056 A3       8/2001
(Continued)

*Primary Examiner* — Tarifur Chowdhury
*Assistant Examiner* — Md M Rahman
(74) *Attorney, Agent, or Firm* — Reinhart Boerner Van Deuren P.C.

(57) ABSTRACT

The invention concerns an apparatus for inspection of products (3', 3"), provided with a transport mechanism (2) configured to transport a continuous stream of products (3', 3") so that, on leaving the transport mechanism, the product stream (3', 3") follows a free-fall path along which it is fed in a single product layer through an inspection zone (16), which has a length (L) that at least corresponds to the width of the aforementioned single product layer, a light source (5, 5') configured to illuminate said inspection zone (16), a detection unit (6), configured to optically scan the illuminated inspection zone (16), an analysis unit (17) and possibly a removal unit (7) and also a background element (10'), which is situated behind the falling product stream, seen from the position of the detection unit, positioned so that:—light beams from the light source impinge on an illumination zone (14) of the background element when these beams do not impinge on a product from the product stream (3', 3"),—the detection unit can only receive an image of a detection zone (13) of the background element, characterized in that the background element is mounted so that the illumination zone (14) and the detection zone (13) are separated from each other.

18 Claims, 4 Drawing Sheets

(51) Int. Cl.
*B07C 5/342* (2006.01)
*B07C 5/36* (2006.01)
*G01N 21/84* (2006.01)

(56) References Cited

U.S. PATENT DOCUMENTS

| | | | |
|---|---|---|---|
| 7,113,272 B2 | 9/2006 | Bourely et al. | |
| 2002/0007573 A1* | 1/2002 | Sueshige | 37/244 |
| 2007/0039856 A1* | 2/2007 | Adams et al. | 209/644 |
| 2007/0187035 A1 | 8/2007 | To et al. | |
| 2010/0096299 A1* | 4/2010 | Adams et al. | 209/577 |

FOREIGN PATENT DOCUMENTS

| | | |
|---|---|---|
| DE | 10 2004 021 689 A1 | 11/2005 |
| EP | 0 443 769 A2 | 2/1991 |
| EP | 1 449 630 A1 | 8/2004 |
| EP | 1 726 372 A1 | 11/2006 |
| GB | 2042717 | 9/1980 |
| JP | 1-111481 | 4/1989 |

\* cited by examiner

OPTICAL INSPECTION APPARATUS AND OPTICAL SORTING APPARATUS

TECHNICAL FIELD

This application concerns machines for continuous inspection as well as machines for continuous sorting of a stream of products, such as bulk products, which are transported past an inspection unit in a single layer, these products preferably being inspected for their optical properties.

The application especially concerns a setup of the optical system in order to solve the problem of background detection in a simple and cost-effective manner.

PRIOR ART

Machines for inspection and sorting of bulk products supplied in a continuous stream are known. Such inspection machines comprise a feed unit, an optical system and an analysis unit. A sorting machine also has a removal unit and a discharge unit.

The feed unit supplies a stream of products which are to be inspected continuously through an inspection zone that is scanned by the optical system, which is in operational communication with the analysis unit. The analysis unit analyzes each separate product in the product stream for one or more preselected properties, such as color, shape and/or texture or any combination thereof. Based on this analysis, the analysis unit can examine whether the inspected product satisfies specific criteria in terms of the observed property(ies), resulting in a classification. In the case of a sorting machine the products that belong to a specific class or combination of classes are removed from the product stream by means of the removal unit, controlled for this purpose by the analysis unit. The incoming product stream is thereby separated into a first product stream of removed products and a second product stream of unremoved products.

An example of such a sorting machine is described in European patent application EP 1 726 372 A1, especially in FIG. 1. The feed unit comprises a conveyor belt or vibrating table followed by a chute. The products leave the conveyor belt with a slight forward speed, but on sliding over this chute will accelerate under the influence of gravity. The products leave the chute with a velocity vector determined by the curvature and arrangement of this chute. Analysis and subsequent removal of these products occurs when these products are moving substantially in the vertical direction. Such types of sorting machines are known as free-fall sorting machines.

On leaving the chute, the products are scanned by a laser beam. The light beams impinging on the products are partly reflected and picked up by a sensor that converts this light to an electrical signal, which can then be processed in an analysis unit.

The removal unit consists of a number of air valves that can be controlled individually by the analysis unit. A product that is blown out in this way is trapped in a duct that discharges into a transport mechanism, typically a vibrating gutter, which diverts the product.

Another type of inspection and sorting machine is shown in U.S. Pat. No. 4,889,241. This concerns a so-called belt machine, which does not comprise a chute, but in which the products are supplied in a single layer on a moving belt with a given speed. Products that reach the end of the belt follow a path through the air with a (generally horizontal) initial speed equal to the belt speed. The detection and removal unit is situated above or beneath the single layer of products after they have left the belt. Products to be removed are removed from the stream, the other products go to a second conveyor belt or to a chute.

A requirement for such inspection and sorting apparatuses, especially the optical sensor and analysis device, is that a correct distinction can be made between optical information coming from the inspected products and optical information coming from the background.

Use of a background element is known for this purpose. European patent application EP 0 443 769 A2, for example, describes a sorting machine with a background element positioned in the view of the camera and whose color corresponds to the color of the good product. Because of this the signals are independent of the size of the product and they only comprise information concerning deviating color. It is necessary in this case that the background element be illuminated with the same illumination used to illuminate the product stream.

Belgian patent BE 1013056 describes an active background element practically designed as a cylindrical roll which permanently emits light itself, preferably of a wavelength of the same order of magnitude as the light emitted by the products being treated.

A requirement of existing systems is therefore that the background element exhibits the optical properties of the products being treated. If the products to be treated are characterized by a high number of optical properties, practical design of such a background element is a problem. For example, if the products being treated are characterized by a hyperspectral pattern that consists of 320 measured points, a person skilled in the art would have to make a background element that satisfies this pattern almost exactly.

SUMMARY OF THE INVENTION

The invention concerns an apparatus as disclosed in the appended claims. The invention teaches a simple and cost-effective arrangement of the optical system, which permits optical information originating from inspected products and optical information originating from the background to be distinguished from each other in an efficient and correct manner in the analysis unit. In particular, the invention concerns an inspection apparatus and a sorting apparatus with such an arrangement of the optical system.

In particular, this invention teaches an arrangement of a hyper- or multispectral camera, in which the background signal can be detected in a simple and cost-effective manner.

The invention therefore concerns an apparatus for inspection of products comprising the following components:
  a transport mechanism configured to transport a continuous stream of products so that the product stream, after leaving the transport mechanism follows a free-fall path, along which it is fed in a single product layer through an inspection zone, having a length that at least corresponds to the width of the aforementioned single product layer,
  a light source configured to illuminate said inspection zone,
  a detection unit, configured to optically scan the illuminated inspection zone,
  an analysis unit in operational connection with the detection unit and which is arranged to process and analyze the optical information that it receives from the detection unit according to well-defined criteria,
  a background element, which is situated behind the falling product stream, seen from the position of the detection unit, positioned so that:

light beams from the light source only impinge on an illumination zone of the background element when these beams do not impinge on a product from the product stream, the detection unit can only receive an image of a detection zone of the background element, characterized in that the background element is mounted so that the illumination zone and the detection zone are separated from each other According to a specific embodiment:

the light source is configured so that light beams coming from said light source are focused so that said light beams are bundled at the level of inspection zone on a line, or at least in a narrow strip, which extends over the entire length of the inspection zone and wherein the illumination zone is formed by a strip of the background element, the detection unit is a camera configured so that the camera can only detect a strip of the background element, wherein said strips of the background element do not overlap each other.

According to another embodiment, the light source is a laser source configured to illuminate the inspection zone with a laser beam that scans this zone repeatedly in the length direction of this zone and in which the detection unit comprises at least one light sensor, which can receive laser light that is reflected off a falling product or off the background element.

The background element may be separated from the ambient light and may be formed by the rear wall of a duct in which products are discharged after the inspection zone.

An apparatus according to the invention can also be provided with a removal unit, configured to remove rejected products from the product stream. The background element in this apparatus can be formed by the rear wall of a discharge duct along which rejected products are discharged.

The detection unit can be a multispectral or hyperspectral camera.

An apparatus according to the invention can comprise more than one light source and/or more than one detection unit, in which case the respective illumination zones and detection zones of these sources and detection units are separated from each other.

According to one embodiment, the transport mechanism comprises a chute, configured to guide said product stream during its fall so that when the product stream leaves the guide plate it follows a free-fall path along which it is fed in a single product layer through the inspection zone.

According to another embodiment, the transport mechanism comprises a conveyor belt, configured to eject said product stream in the form of a single layer, which is fed through the inspection zone.

DETAILED DESCRIPTION OF THE INVENTION

The present invention will be described by means of some examples referring to certain figures without any limiting character. The figures are only schematic and non-limiting. Dimensions of certain elements can be exaggerated or not to scale in the figures. However, this is for illustrative reasons. The dimensions and relative dimensions therefore do not necessarily correspond to reality.

Figure 1:
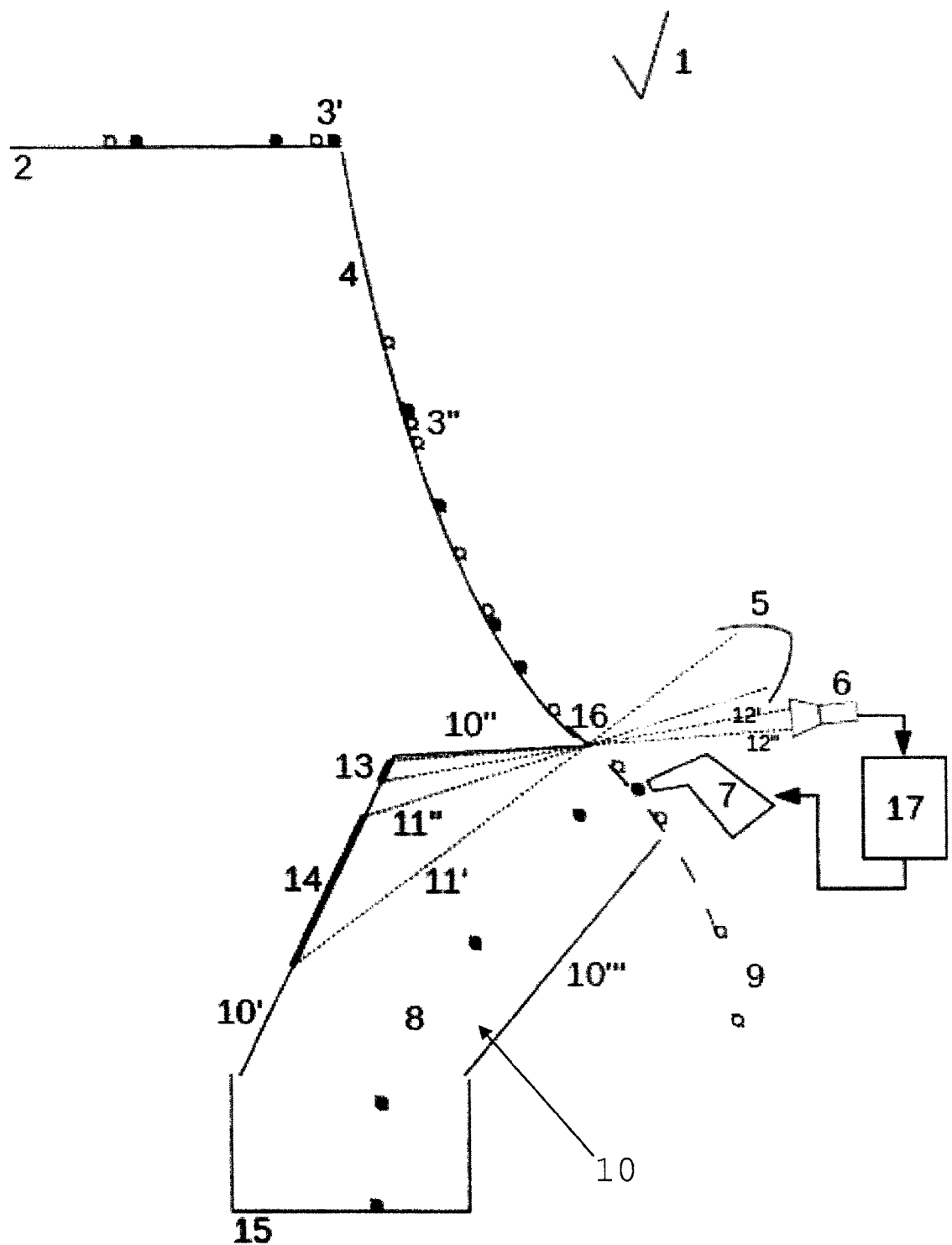
FIG. 1 shows a side view of a free-fall optical sorting apparatus according to the invention for the continuous processing of a single stream of products.

FIG. 1 shows a possible embodiment of an apparatus according to the invention for sorting of a continuous stream of products 3', 3". This is an example of a so-called 'free-fall' apparatus. The apparatus comprises the following components: a transport mechanism, which includes a conveyor belt or vibrating plate 2 and a chute 3. The conveyor belt or vibrating plate 2 transports a continuous stream consisting of a single layer of products 3', 3" to the guide plate 4 which supports said product stream 3', 3" during its fall so that, on leaving the guide plate, the product stream 3', 3" follows a free-fall path along which it is fed in a single product layer (being a layer whose thickness almost corresponds to (i.e. is no higher than) the thickness of one product) of specified width (perpendicular to the plane of the figure) through an inspection zone 16. The product stream comprises products (3') to be removed and products (3") to be selected. The aforementioned inspection zone 16, which has a length L that at least corresponds to the width of the aforementioned single product layer, is illuminated with a light source 5. The inspection zone 16 illuminated in this way is optically scanned by means of a camera 6. Operationally connected to this camera 6 is an analysis unit 17 is, which processes and analyzes the optical information received from camera 6 according to well-defined criteria. In this way, the products in the product stream 3', 3" can be evaluated by the analysis unit 17 for possession of well-defined optical properties. The analysis unit 17 can then activate a removal mechanism 7 as a function of the detected optical properties, which removes the products from the product stream 3', 3", preferably by means of air valves, as known in the prior art. The original product stream 3', 3" is separated thereby into a first product stream 8, which consists of products 3' that are removed by the removal mechanism 7 from the original product stream 3', 3" and a second product stream 9, which consists of products 3" that have been able to continue their normal free-fall trajectory during the entire sorting process.

The first separated product stream 8 is collected in a discharge duct 10 with side walls 10', 10", 10''' that discharge into a vibrating gutter 15 that conveys the product stream 8 further. The rear wall 10' of the duct functions as background element, i.e., an element situated behind the falling product stream, seen from the position of the camera. Light beams that are not reflected by falling products impinge on the background element (in other words light beams that impinge on a location of the inspection zone 16 where no product is present). As shown in the figures, the light source 5 and the detection unit 6 on the one hand, and the background element on the other hand, are situated on opposite sides of inspection zone 16.

The light beams 11', 11" coming from aforementioned light source 5 are focused so that said light beams 11', 11" are bundled at the level of the inspection zone 16 on a line, at least in a narrow strip, which extends over the entire length L of the inspection zone 16. Light beams that are not interrupted by a falling product 3' or 3" diverge behind the inspection zone 16 to finally impinge on a strip 14 of the rear wall 10', hereafter referred to as the illumination zone 14. This zone is the only area of the background element that can receive light from the light source 5.

Figure 2:
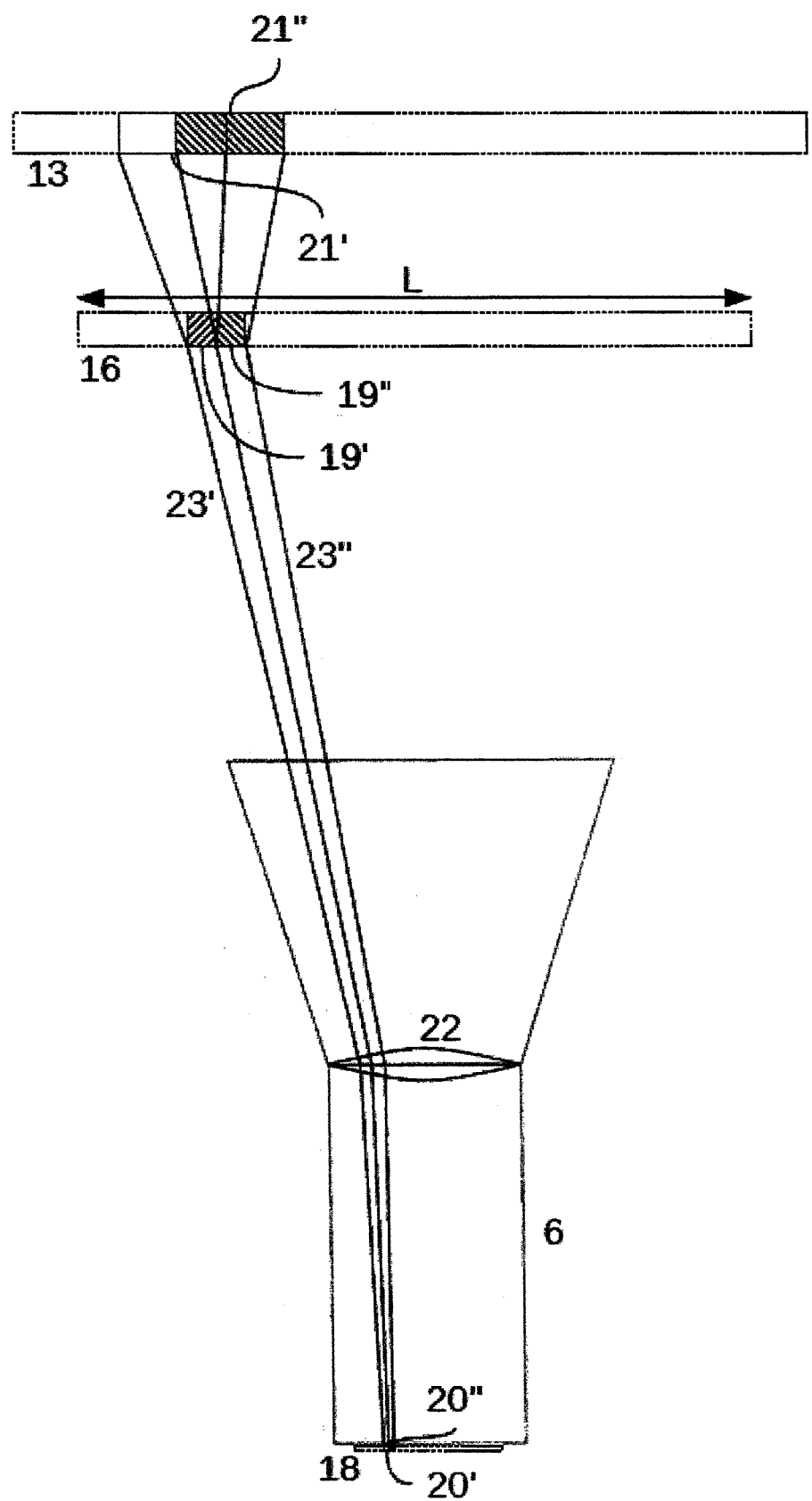
FIG. 2 shows how each individual pixel on the camera sensor corresponds to a small rectangular area in the focused inspection zone of a sorting apparatus. A corresponding area can also be marked out in the unfocused zones behind the inspection zone.

The camera 6 comprises a camera lens 22 (see FIG. 2), which focuses the received light 23', 23" at the level of a camera sensor 18. The camera sensor 18 consists of a number of pixels, which are arranged either on a line or in a two-dimensional pattern. Each individual pixel 20', 20" corresponds to a well-defined rectangular area 19', 19" in the inspection zone 16. The individual pixels are read out at an established rhythm and sent to the analysis unit 7.

When a product is situated in inspection zone 16, the pixels that correspond to that product contain optical information concerning said product.

At locations 19', 19" in the inspection zone 16, where no products are present, the corresponding pixels 20', 20" will contain optical information about corresponding areas 21', 21" in a strip 13 of the rear wall 10', hereafter referred to as the detection zone 13, which extends behind inspection zone 16. The camera is focused on the inspection zone 16 (in other words, receives light beams 12', 12" reflected by products situated in the inspection zone). Because of this the detection zone 13 is not imaged in focused fashion on the camera sensor 18 and bordering pixels 20', 20" will contain information about overlapping areas 21', 21" in the detection zone 13. The detection zone 13 is also the only area of the background element from which the camera can receive light.

It is important in the context of optical inspection and sorting that a clear distinction can be made between pixels that belong to products, on the one hand, and pixels that do not belong to products, on the other hand, in other words those belonging to the background. It is important in fact that pixels that do not belong to products cannot adversely affect the sorting process. This could be the case if the analysis unit 17 were to classify these background pixels in a class that is arranged for further removal from the product stream 3', 3".

This application describes various possible embodiments of an inspection system and sorting apparatus 1, which permit in simple and cost-effective fashion a clear distinction to be made in the analysis unit 17 between pixels that belong to products, on the one hand, and pixels that do not belong to products, on the other hand, in other words, pixels that belong to the background.

It is characteristic for an apparatus according to the invention that the light source 5 and the camera 6 are arranged so that the aforementioned detection zone 13 does not overlap the aforementioned illumination zone 14. In that case the detection zone 13 will not be illuminated and pixels corresponding to it will not receive any light. These pixels, in other words, will be uniformly black. This results in a simple and efficient system to distinguish object pixels and non-object pixels from each other.

It is furthermore advantageous to make use of light shielding that prevents the detection zone 13 from being illuminated or disturbed by external light sources, like the sun.

This can preferably be achieved by having the duct 10, on the one hand, function as a light shield and, on the other hand, as a discharge duct. In this way a compact unit is obtained with a minimum of mechanical structural elements.

In an advantageous variant the inside of the duct 10, at least the rear wall 10', is made black, for example by ionizing the metal black.

Figure 3:
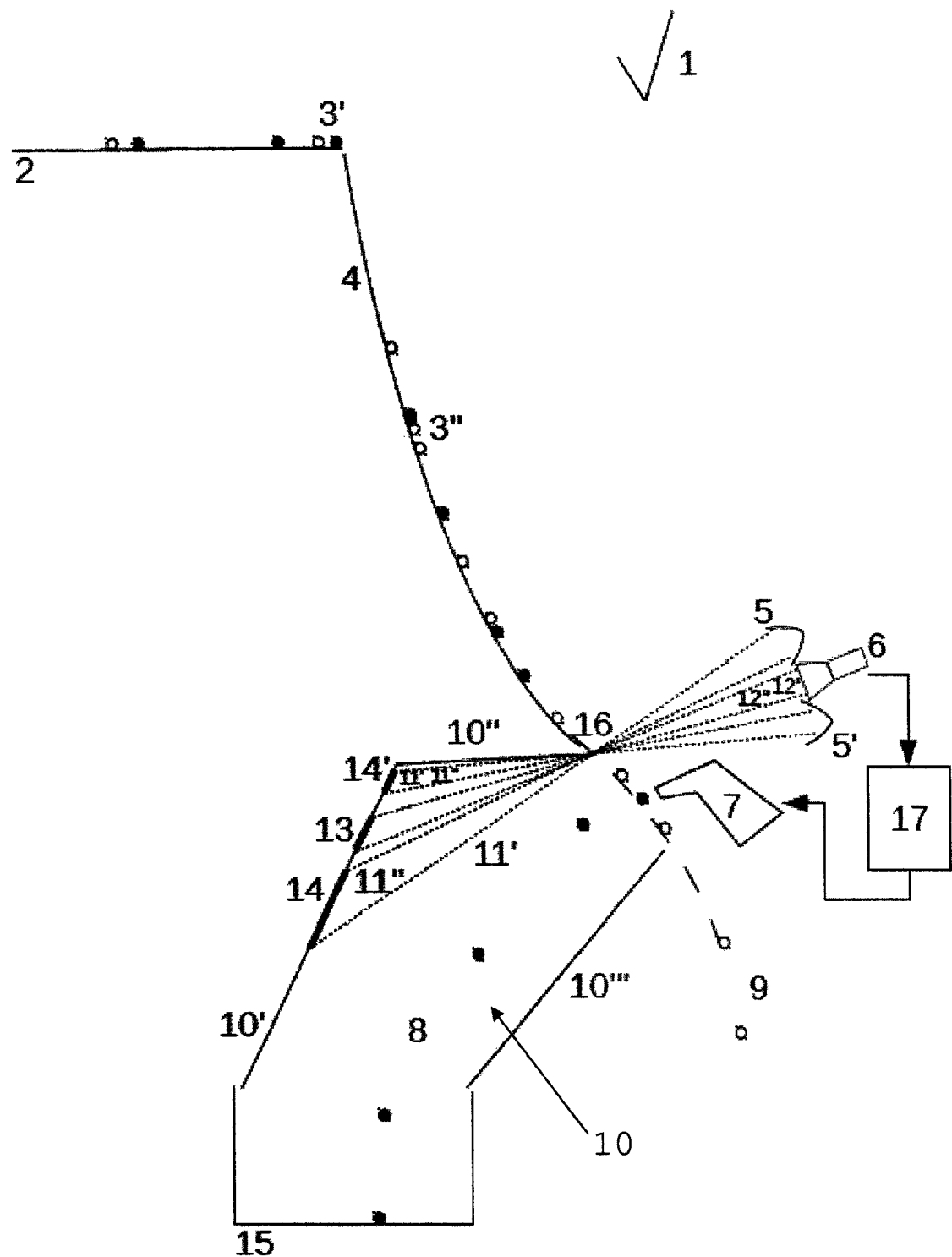
FIG. 3 shows an apparatus according to the invention provided with two light sources.

FIG. 3 shows an embodiment according to the invention in which two light sources are provided. The light beams 11', 11" coming from light sources 5, 5' are focused so that the aforementioned light beams 11', 11" are bundled at the level of the inspection zone 16 in a line, at least in a narrow strip, which extends over the entire length L of the inspection zone 16. The light beams 11', 11" diverge behind this inspection zone 16 to finally impinge on the respective illumination zones 14 and 14' at the level of the rear wall 10' of the discharge duct 10.

The camera 6 is mounted so that said detection zone 13 does not overlap said illumination zones 14, 14'. In this case the zone 13 will not be illuminated and pixels corresponding to it will not receive any light. These pixels, in other words, will be uniformly black. This results in a simple and efficient system to distinguish object pixels and non-object pixels from each other.

A person skilled in the art realizes that an arrangement according to the invention can also consist of different cameras and/or different light sources. It is essential here that the illuminated zones 14 do not overlap the detection zones 13 that coincide with the respective visual fields of the mounted cameras 6.

The illumination 5, 5' can consist of fluorescent tubes, halogen bulbs or any other static illumination arranged over the full length of the inspection zone 16.

The illumination 5, 5' can also consist of a series of LEDs arranged over the full length of the inspection zone 16. LEDs of different wavelengths can be mounted in alternated fashion in order to obtain illumination consisting of said different wavelengths. The LEDs of different wavelengths can also be controlled in alternated fashion. Such illumination is monochromatic in a well-defined period that can be tuned to the recording speed of the camera 6.

The camera 6 can be a line scanning camera, which makes a complete recording per scan of the inspection zone 16. Most commonly these cameras use sensors of the CMOS or CCD type. The invention, however, is not limited to this type of camera.

The camera 6 can also consist of a scanning apparatus, for example a rotating multifaceted mirror, which scans the inspection zone 16 in a temporal sawtooth movement. The light sensor can then consist of a photon multiplier tube (PMT), an avalanche diode or the like, which is sampled to thereby result in the aforementioned pixels 20', 20". Such an apparatus is typically used in combination with one or more laser sources.

The inspection apparatus according to the invention works most advantageously in the case in which the camera 6 is a so-called multispectral or hyperspectral camera. In this case the camera 6 consists of a spectrograph in combination with a focal-plane sensor. The spectrograph breaks the incoming light into a spectrum that is then projected on said focal-plane sensor. This sensor consists of a matrix of pixels in which pixels along one direction contain spectral content and pixels in the other direction contain spatial information. In other words a pixel at location (x, s) in the matrix contains the spectral response at frequency s at the level of position x in the inspection zone 16. An object that is measured by means of a multi- or hyperspectral sensor results in a spectral pattern that is indicative for the chemical composition of said object. When using a multispectral or hyperspectral sensor in combination with a background element that corresponds to the products to be accepted, this background element not only would have to have the same color as the products to be accepted, but also the same chemical composition, which is not possible or very difficult to achieve. The invention therefore offers a particularly good solution when using this type of sensor.

Figure 4:
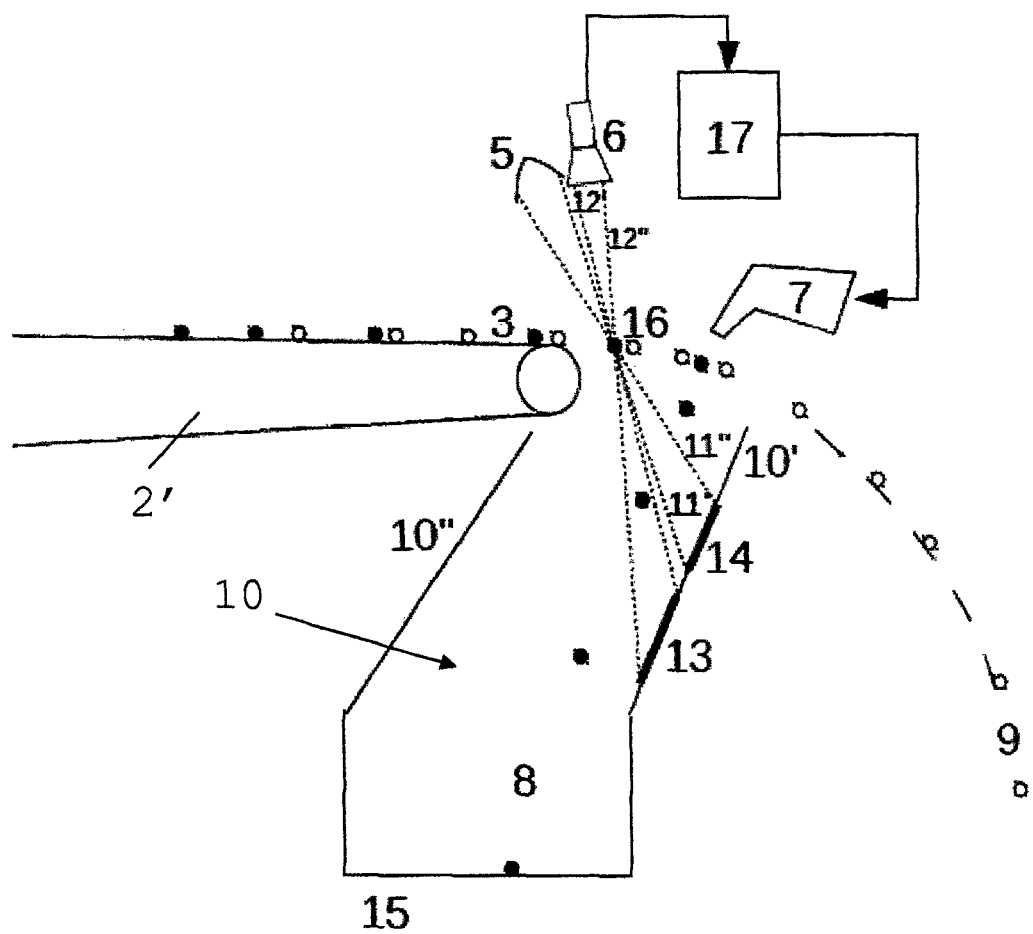
FIG. 4 shows a belt apparatus produced according to the invention.

A person skilled in the art will realize that an inspection system according to the invention can also be effective on an apparatus in which the aforementioned product stream 3', 3" is supplied via transport devices such as a belt or hopper. An example of a belt apparatus is shown in FIG. 4. The same numbering is used for components that are identical or have the same function as the components shown in FIG. 1. This apparatus comprises a transport mechanism consisting of a conveyor belt 2', which moves at a higher speed than the conveyor belt 2 in the free-fall apparatus so that the products are ejected from the belt with an initial horizontal speed and then follow a parabolic falling path. The light source 5 and camera 6 are now arranged above the falling path. The products to be removed are removed by the removal mechanism 7 and enter the discharge duct 10 with side walls 10' and 10". In this case the side wall 10' positioned opposite the conveyor belt plays the role of background element. Here again this side wall is arranged so that the detection zone 13 and the illumination zone 14 do not overlap each other.

The invention claimed is:

1. An apparatus for inspection of products (3', 3") comprising the following components:
    a transport mechanism (2, 4; 2') configured to transport a continuous stream of products (3', 3") so that the product stream (3', 3"), after leaving the transport mechanism follows a free-fall path, along which it is fed in a single product layer through an inspection zone (16);
    wherein the inspection zone has a length (L) that at least corresponds to the width of the aforementioned single product layer,
    a light source (5, 5') configured to illuminate said inspection zone (16),
    a detection unit (6), configured to optically scan the illuminated inspection zone (16),
    an analysis unit (17) in operational connection with the detection unit and which is arranged to process and analyze the optical information that it receives from the detection unit according to well-defined criteria,
    a background element (10'), which is situated behind the falling product stream, seen from the position of the detection unit, positioned so that:
    light beams from the light source only impinge on an illumination zone (14) of the background element when these beams do not impinge on a product from the product stream (3', 3"),
    the detection unit can only receive an image of a detection zone (13) of the background element, characterized in that the background element is mounted so that the illumination zone (14) and the detection zone (13) are separated from each other;
    wherein the light source (5) is configured so that light beams (11', 11") coming from said light source are focused so that said light beams are bundled at the level of inspection zone (16) on a line, or at least in a narrow strip, which extends over the entire length (L) of the inspection zone (16) and wherein the illumination zone (14) is formed by a strip of the background element (10');
    wherein the detection unit is a camera (6) configured so that the camera can only detect a strip (13) of the background element; and
    wherein said strips (13, 14) of the background element do not overlap each other.

2. The apparatus according to claim 1, in which the background element (10') is separated from the ambient light.

3. The apparatus in claim 2, wherein the background element (10') is formed by the rear wall of a duct in which products are discharged after the inspection zone (16).

4. The apparatus according claim 1, which is also provided with a removal unit (7) configured to remove rejected products from the product stream.

5. The apparatus according to claim 4, wherein the background element (10') is formed by the rear wall of a discharge duct (10), along which rejected products are discharged.

6. The apparatus according to claim 1, wherein the camera is a multispectral or hyperspectral camera.

7. The apparatus according to claim 1, comprising more than one light source (5, 5') and/or more than one detection unit (6, 6') and in which the respective illumination zones (14) and detection zone (13) of these light sources and detection units are separated from each other.

8. The apparatus according to claim 1, wherein the transport mechanism comprises a chute (4), configured to guide said product stream during its fall so that when the product stream (3', 3") leaves the guide plate it follows a free-fall path along which it is fed in a single product layer through the inspection zone (16).

9. The apparatus according to claim 1, in which the transport mechanism comprises a conveyor belt (2), configured to eject said product stream in the form of a single layer, which is fed through the inspection zone (16).

10. An apparatus for inspection of products (3', 3") comprising the following components:
    a transport mechanism (2, 4; 2') configured to transport a continuous stream of products (3', 3") so that the product stream (3', 3"), after leaving the transport mechanism follows a free-fall path, along which it is fed in a single product layer through an inspection zone (16);
    wherein the inspection zone has a length (L) that at least corresponds to the width of the aforementioned single product layer,
    a light source (5, 5') configured to illuminate said inspection zone (16),
    a detection unit (6), configured to optically scan the illuminated inspection zone (16),
    an analysis unit (17) in operational connection with the detection unit and which is arranged to process and analyze the optical information that it receives from the detection unit according to well-defined criteria,
    a background element (10'), which is situated behind the falling product stream, seen from the position of the detection unit, positioned so that:
    light beams from the light source only impinge on an illumination zone (14) of the background element when these beams do not impinge on a product from the product stream (3', 3"),
    the detection unit can only receive an image of a detection zone (13) of the background element,
    characterized in that the background element is mounted so that the illumination zone (14) and the detection zone (13) are separated from each other; and
    wherein the light source is a laser source configured to illuminate the inspection zone (16) with a laser beam that scans this zone repeatedly in the length direction of this zone and in which the detection unit comprises at least one light sensor, which can receive laser light that is reflected off a falling product (3', 3") or off the background element (10').

11. The apparatus according to claim 10, in which the background element (10') is separated from the ambient light.

12. The apparatus in claim 11, wherein the background element (10') is formed by the rear wall of a duct in which products are discharged after the inspection zone (16).

13. The apparatus according claim 10, which is also provided with a removal unit (7) configured to remove rejected products from the product stream.

14. The apparatus according to claim 10, wherein the background element (10') is formed by the rear wall of a discharge duct (10), along which rejected products are discharged.

15. The apparatus according to claim 10, wherein the detection unit (6) is a multispectral or hyperspectral camera.

16. The apparatus according to claim 10, comprising more than one light source (5, 5') and/or more than one detection unit (6, 6') and in which the respective illumination zones (14) and detection zone (13) of these light sources and detection units are separated from each other.

17. The apparatus according to claim 10, wherein the transport mechanism comprises a chute (4), configured to guide said product stream during its fall so that when the product stream (3', 3") leaves the guide plate it follows a free-fall path along which it is fed in a single product layer through the inspection zone (16).

18. The apparatus according to claim 10, in which the transport mechanism comprises a conveyor belt (2), configured to eject said product stream in the form of a single layer, which is fed through the inspection zone (16).

\* \* \* \* \*